(12) United States Patent
Ravid et al.

(10) Patent No.: US 6,256,093 B1
(45) Date of Patent: Jul. 3, 2001

(54) ON-THE-FLY AUTOMATIC DEFECT CLASSIFICATION FOR SUBSTRATES USING SIGNAL ATTRIBUTES

(75) Inventors: Erez Ravid, Jerusalem; Ido Holcman; Vladimir Mikolinsky, both of Rechovot, all of (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/104,226

(22) Filed: Jun. 25, 1998

(51) Int. Cl.$^7$ .................................................. G01N 21/00
(52) U.S. Cl. ................................... 356/237.2; 356/237.4; 356/237.5
(58) Field of Search ............................. 356/237.1, 237.2, 356/237.4, 237.3, 237.5; 250/559.42, 559.48; 382/149, 159; 348/125, 126

(56) References Cited

U.S. PATENT DOCUMENTS

| | | | |
|---|---|---|---|
| Re. 33,991 | * 7/1992 | Shiba et al. | 356/237.3 |
| 4,253,768 | * 3/1981 | Yaroshuk et al. | 356/237.1 |
| 4,587,617 | * 5/1986 | Barker et al. | 356/237.5 |
| 4,626,101 | * 12/1986 | Ogawa et al. | 356/237.2 |
| 5,544,256 | * 8/1996 | Brecher et al. | 382/149 |
| 5,669,447 | 9/1997 | Walker et al. | 166/300 |
| 5,699,447 | 12/1997 | Alumot et al. | |
| 5,712,701 | * 1/1998 | Clementi et al. | 356/237.2 |
| 5,798,830 | * 8/1998 | Srinivasan | 356/237.2 |
| 5,801,965 | * 9/1998 | Takagi et al. | 356/237.1 |
| 5,875,027 | * 2/1999 | Ishiguro et al. | 356/243.4 |

FOREIGN PATENT DOCUMENTS

| | | |
|---|---|---|
| 4-152545 | 5/1992 | (JP). |
| 96/39619 | 12/1996 | (WO). |
| 97/46865 | 12/1997 | (WO). |

OTHER PUBLICATIONS

PCT Written Opinion dated Mar. 23, 2000.
XP–002119842; Alumot et al., "Dual sensor technology for high–speed detection of 0.1 micron defects," Proceedings of the Spie—The International Society for Optical Engineering, vol. 1926, pp. 570–581; 1993.
XP–002119843; Carmel et al., "New Directions in Process Control," Proceedings of the Spie—The International Society for Optical Engineering, vol. 2196, pp. 332–340; 1994.

* cited by examiner

*Primary Examiner*—Hoa Q. Pham
(74) *Attorney, Agent, or Firm*—Sughrue, Mion, Zinn, Macpeak & Seas PLLC (57) ABSTRACT

A system for on-the-fly automatic defect classification (ADC) in a scanned wafer. The system includes a light source illuminating the scanned wafer so as to generate an illuminating spot incident on the wafer. Sensor collecting light scattered from the spot by the at least two spaced apart detectors, and processor analyzing the collected light so as to detect defects in the wafer and classifying the defects into distinct defect types.

41 Claims, 10 Drawing Sheets

ON-THE-FLY AUTOMATIC DEFECT CLASSIFICATION FOR SUBSTRATES USING SIGNAL ATTRIBUTES

FIELD OF THE INVENTION

The present invention is in the general field of detecting and classifying defects in wafers during and/or after manufacture.

BACKGROUND OF THE INVENTION

As is well known, considerable effort is spent in academia and industry towards developing techniques enabling the detection of defects in wafers before their cleavage into distinct dies, capsulation and subsequent distribution to the marketplace in the form of chips. Preliminary defect detection inter alia improves the "yield" in terms of discarding defective wafers and consequently increasing the percentage of fault-free chips delivered from the production line.

In recent years, defect detection has been improved by techniques for classifying defects into distinct defect types. These techniques not only allow identification of defective wafers so as to increase the yield, but also to provide some information on the cause of the defects. The production stage can then be reconfigured or modified in order to produce a better wafer series.

Figure 1:
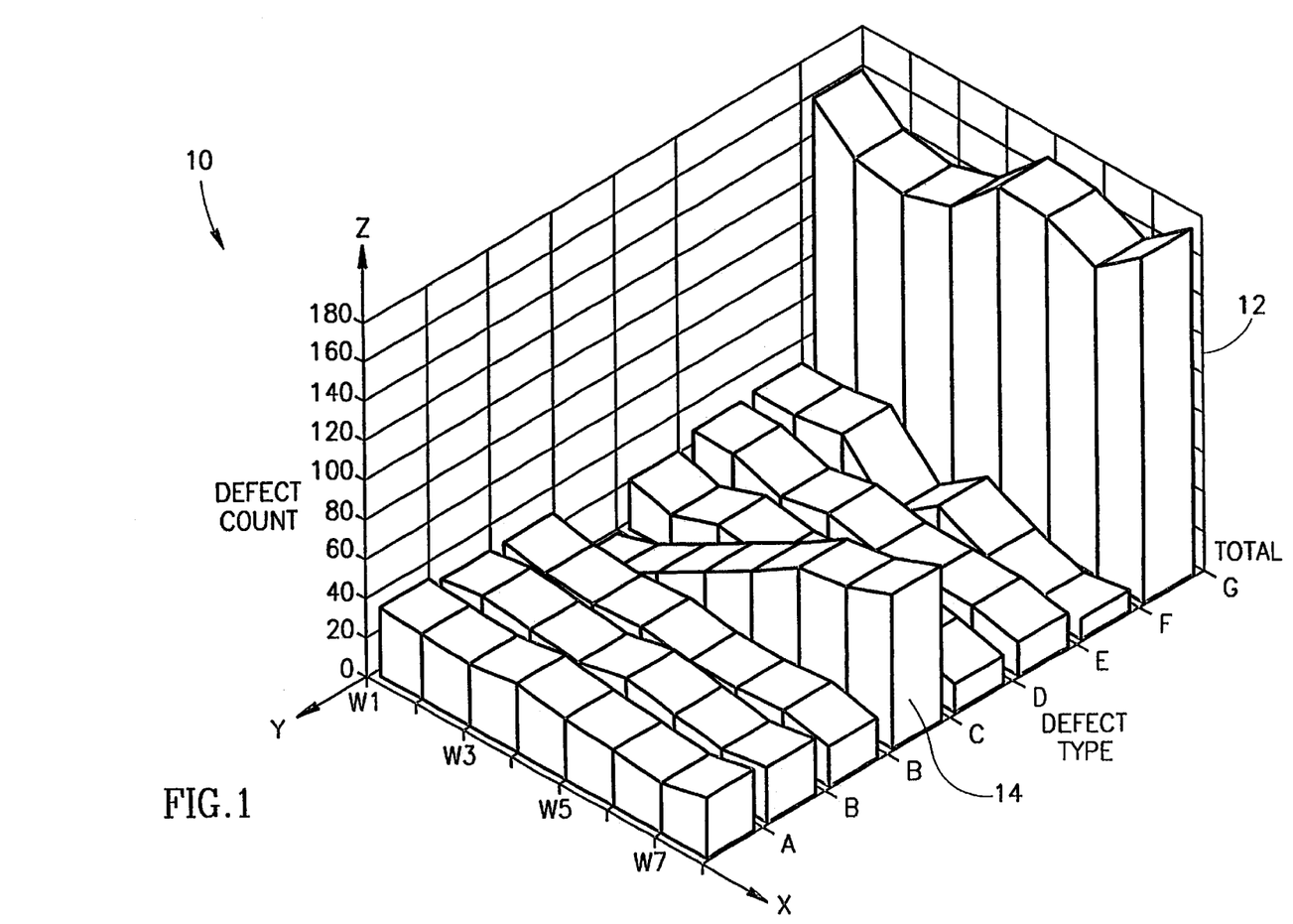
FIG. 1 is a three dimensional graph that illustrates the advantages of defect classification.

The improved sensitivity accomplished by classifying defects is illustrated graphically in FIG. 1 (10), which shows the number of defects (Z) of various types (Y) for four sequentially produced wafers (X). Whilst the total count (12) is essentially the same for the four wafers, the count for defect type D (14) dramatically increased over time. This allows the cause of the defect to be identified and corrected.

A rudimentary defect classification method involves a person visually inspecting wafers for defects and classifying the defects according to predetermined criteria. This manual procedure is not only slow but also error prone, since it relies on the inspector's professional skills which obviously differ from one inspector to another.

Automatic Defect Classification (ADC) techniques cope in many respects with the shortcomings of the manual procedures. Thus, for example.

KLA of Santa Clara, Calif., markets a software package, called Impact, as an add-on option to its inspection-review systems, such as the Indy 2230. The software applies certain algorithm to the defect image taken by a CCD camera to attempt and classify the defect. Notably, the Impact algorithm can be operated only when the system is in the review mode, and is inoperable when the system is in the inspection mode. Thus, in order to classify the defects, the system first has to scan the entire wafer in the inspection mode, switch to the review mode and re-visit the suspected sites identified during the inspection mode, take a magnified image of the defect and a reference site, and only then apply the ADC algorithm to classify the defect. The latter mode of operation is generally known in the industry as "re-visit ADC". Also notably, the system uses only a single image of the defect from a single perspective.

Whilst the CCD image based analysis is more accurate and reproducible than the manual procedure (i.e. virtually identical results ate obtained by repeated analysis of the same wafer), it still has some major shortcomings, e.g. it is time consuming. It is important to note in this context that a prolonged wafer inspection session adversely affects the entire production line throughout. Unduly slowing down the production line throughput for wafer inspection is, in many cases, commercially infeasible from a cost perspective, considering the high cost of the chip fabrication process.

There is accordingly, a need in the art to provide for an ADC technique that will provide a relatively accurate and reproducible defect classification, and that at the same time, will substantially reduce the duration of the defect classification stage of hitherto known devices. To this end, in the present invention, defect classification is substantially incorporated into the wafer inspection phase so as to constitute an on-the-fly ADC, i.e. the ADC is inspected as the wafer is scanned for defects.

Throughout this specification, a use is made of the convention that "inspection" refers to the process wherein a substrate is scanned to identify locations suspected of having defects thereon, whilst "review" refers to the process wherein the suspected locations are revisited to confirm/refute the presence of a defect in the suspect location and investigate the defect should such indeed exists, all as known per se.

SUMMARY OF THE INVENTION

The present invention is based on the finding that by illuminating a wafer and collecting the scattered light by at least two detectors it is possible not only to detect defects in the wafer but also to classify the defects into distinct types by analyzing the attributes of the collected light. By this approach, an "on the fly" ADC is accomplished. According to the invention, dark field type detectors are utilized for collecting the scattered light.

Wafer has substantially mirror-like surface and, accordingly, when the illuminating beam is incident on a fault-free region of the inspected wafer it is reflected at expected direction (in compliance with the SNELL law). Thus, by way of example, if the angle of the incident beam is normal to the wafer's surface, the expected direction of the scattered light is also normal to the wafer surface (i.e. the angle between the illuminating beam and the scattered beam is substantially zero). By way of another example if the angle of the incident beam is in 45 relative to the wafer's surface, the expected direction of the scattered light is 135 relative to the wafer surface (i.e. the angle between the illuminating beam and the scattered beam is substantially 90).

Dark field detector is placed such that it is adapted to detect light scattered in direction substantially different from the specified expected direction. Accordingly, when the beam is incident on a fault-free region of the inspected wafer a dark field detector senses low (if any) energy. If, on the other hand, high energy is sensed by a dark field detector, this indicated, that the illuminating beam is not incident on a mirror like surface but rather on an irregular geometry being a defect of a given type. In contrast for bright field detectors an attenuated energy indicates that the illuminating beam is incident on an irregular geometry, whereas high energy indicates that the illuminating beam is not incident on a mirror like surface.

Since dark field detectors respond predominantly to defects (unlike the so called "bright field detectors") they virtually filter out "noise" and respond to "signal" (signal stands for "defect"), and substantially the whole process of defect detection and classification is not only simplified but is also more accurate.

Accordingly, the present invention provides for a method for on-the-fly automatic defect classification (ADC) in a scanned wafer, comprising:

(a) providing at least two spaced apart detectors;

(b) illuminating the scanned wafer so as to generate an illuminating spot incident on the wafer;

(c) collecting light scattered from the spot by the at least two spaced apart detectors; and (d) analyzing said collected light so as to detect defects in said wafer and classifying said defects into distinct defect types.

In the context of the invention, when referring to the location of detectors, this does not necessarily imply that all the constituents of the detector are placed at the prescribed location, but rather that at least the light sensing or collecting part of the detector is placed at the specified location. Thus, for example, by one embodiment, the light receiving edge of a bundle of optic fibers (forming part of a detector) are placed in the vicinity of the wafer whereas the rest of the detector's components are coupled to the opposite remote edge of the bundle.

By one embodiment the illuminating light is incident on the wafer at an angle substantially normal to the wafer surface. According to this embodiment the optical axis of each dark field detector is at a grazing angle to the surface of the inspected wafer.

By another embodiment, the illuminating light is incident on the wafer at a grazing angle to the wafer surface.

By one embodiment, said light detectors are arranged such that each detector faces another detector located substantially opposite thereto.

By another embodiment said detectors are located in substantially even distribution.

The number of dark field detectors may vary depending upon the particular application, e.g. 2 or 4.

"Collecting" may include, whenever required, conversion of the received optical energy to an electrical signal.

By yet another embodiment, at least one additional bright field detector is employed. By this embodiment there is further provided the step of providing at least one additional bright field detector; scattered light being collected by said additional at least one bright field detector according to step (b) and said analysis, stipulated in said step (c), being applied to the scattered light collected by said additional at least one detector.

Preferably said analysis for classifying defects utilizes a so called scattered light attributes. Typical, yet not exclusive, example of attributes being reflected light intensity, reflected light volume, reflected light linearity and reflected light asymmetry. The nature and utilization of the specified reflected light attributes are discussed in greater detail below.

Typical, yet not exclusive, examples of classification types being: small or big particle (substantially a three-dimensional defect); small or big pattern (substantially a two dimensional defect). A refined classification may be used to determine whether the defect is a scratch (big or small). Other defect types may, of course, be used all as required and appropriate, including an unknown defect category.

The present invention further provides for a system for on-the-fly automatic defect classification (ADC) in a scanned wafer, comprising:

(a) light source illuminating the scanned wafer so as to generate an illuminating spot incident on the wafer;

(b) sensor collecting light scattered from the spot by the at least two spaced apart detectors; and (c) processor analyzing said collected light so as to detect defects in said wafer and classifying said defects into distinct defect types.

Still further the invention provides at least one additional bright field detector; said scattered light being collected by said additional at least one bright field detector and said processor applies said analysis to the scattered light collected by said additional at least one detector.

Still further, the invention provides for: in a system for on-the-fly automatic defect classification (ADC) in a scanned wafer, processor programmed to perform the steps comprising:
receiving signals from at least two spaced apart detectors, which signals indicative of light scattered from the wafer and detected by said detectors; and
analyzing said signals so as to detect defects in said wafer and classifying said defects into distinct defect types.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 2:
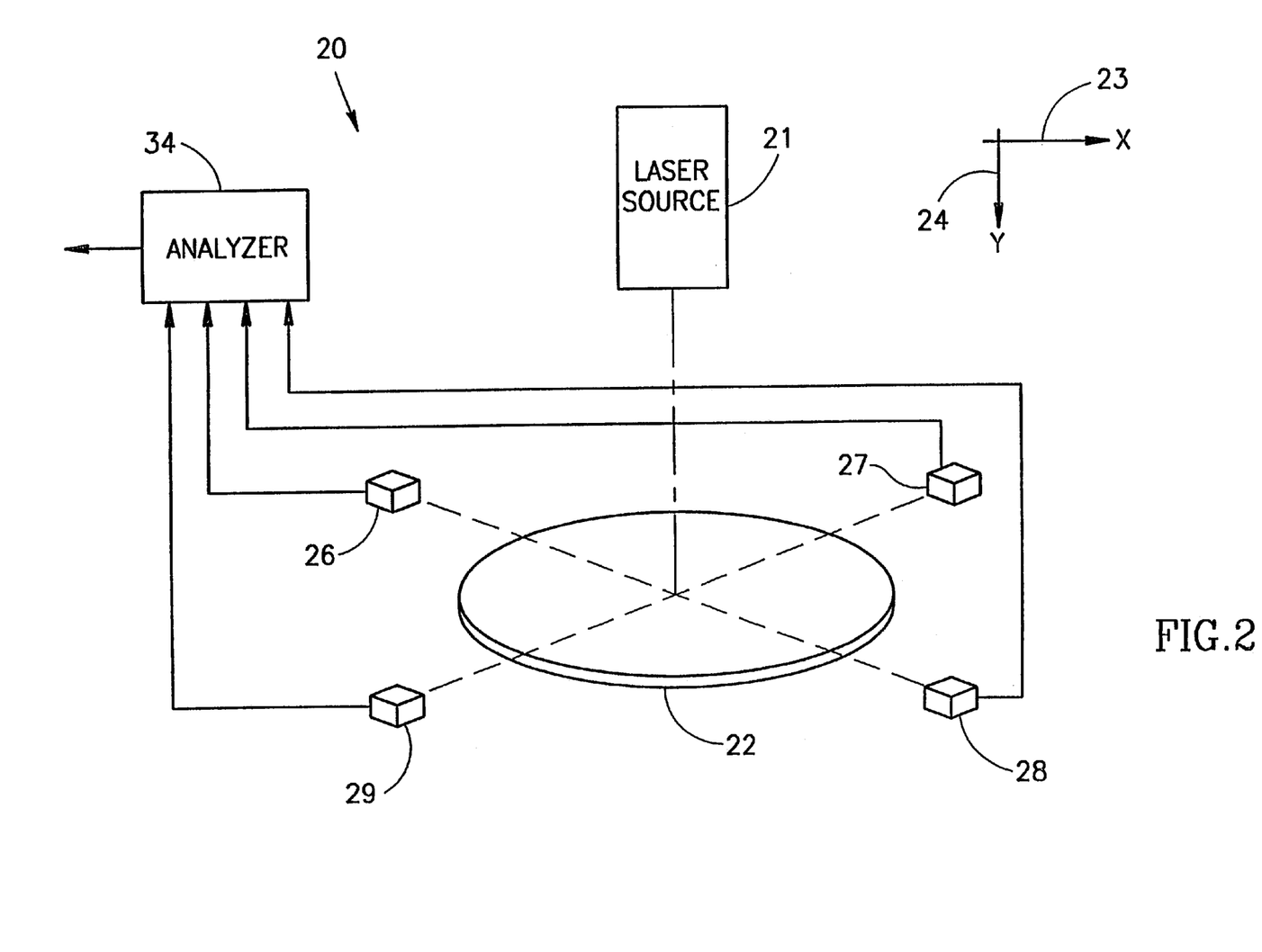
FIG. 2 is a schematic block diagram of a system according to one embodiment of the invention.

Turning first to FIG. 2, there is shown a schematic block diagram of a system (20) according to one embodiment of the invention. As shown, a source of light (21) illuminates a small region of an inspected wafer (22) that is secured to a known per se X-Y stage (not shown). The light source may be, for example, a conventional laser source. The incident light beam continuously scans the wafer in the X direction (arrow 23). At the end of each scan, the wafer is displaced in the Y direction arrow (24), under the control of said X-Y stage, and the wafer is rescanned in the X direction until the entire wafer has been scanned, all as known per se. Four evenly distributed dark field detectors 26, 27, 28 and 29 are placed adjacent to the peripheral edge of the wafer such that their respective fields of view substantially overlap to form the detection zone. The detection zone includes the illuminated region of the wafer, and due to the XY movement of the wafer relative to the detectors, the entire wafer will eventually pass through the detection zone.

Any incident light scattered in the direction of one or more of detectors 26, 27, 28 and/or 29 (e.g. photo multiplier or CCD) will be collected and converted into an electrical signal to be transmitted (typically in digital form) to an analyzer module 34 whose operation will be expounded upon in greater detail below.

Those versed in the art will readily appreciate that FIG. 2 illustrates only one out of many possible embodiments of the invention. Thus, by way of non-limiting example, when considering the detectors of the system, whereas in FIG. 2 four evenly distributed dark field detectors are shown, the invention is by no means bound by e.g. the number of detectors, the location of the detectors and/or their type. Two non-limiting dark field examples are shown also in FIGS. 9 and 10 below.

Figure 3A:
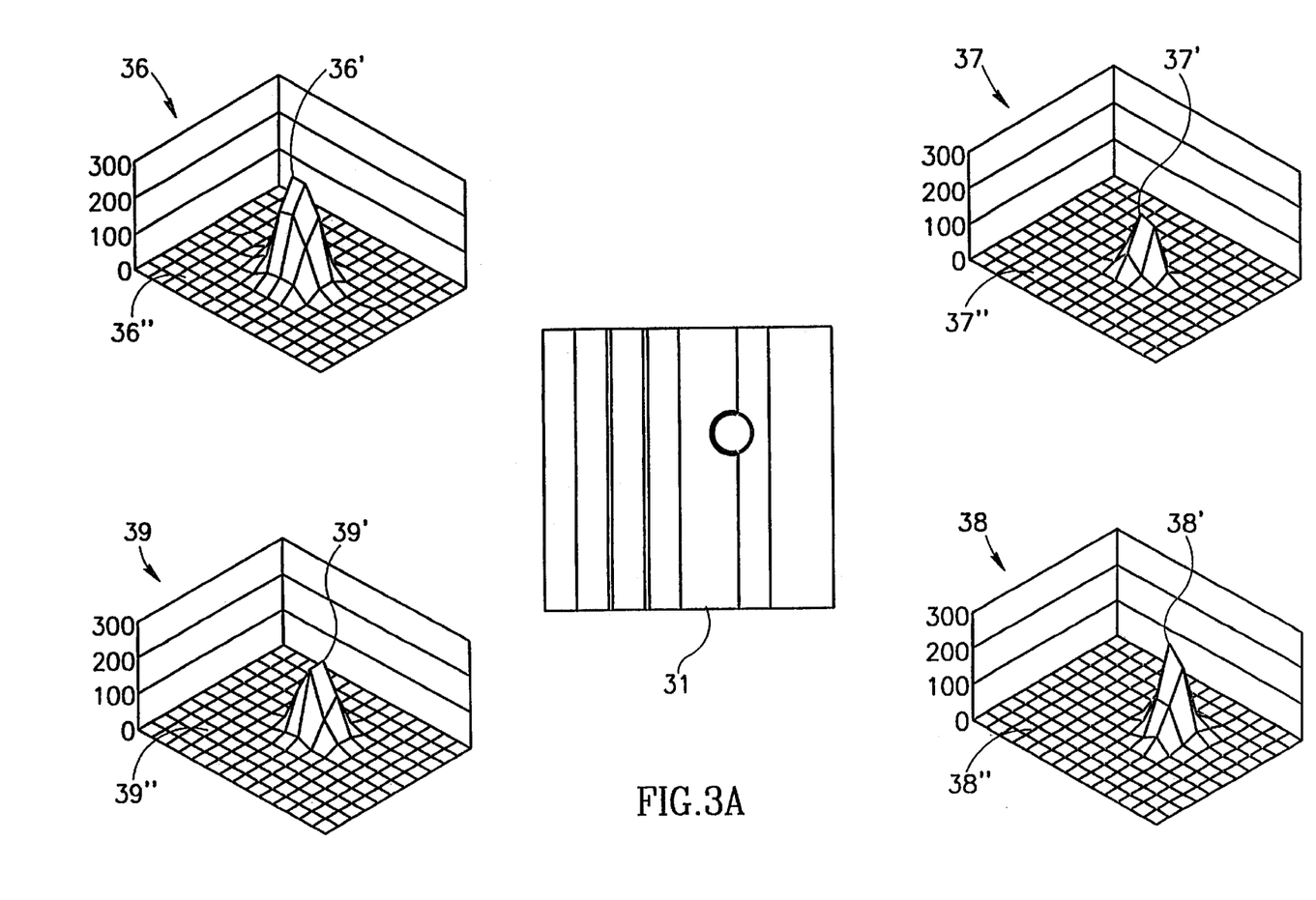
FIGS. 3A and 3B are a graphical representation of a light scattered pattern as detected by respective evenly distributed dark field detectors in response to illuminating a particle type defect.
Figure 3B:
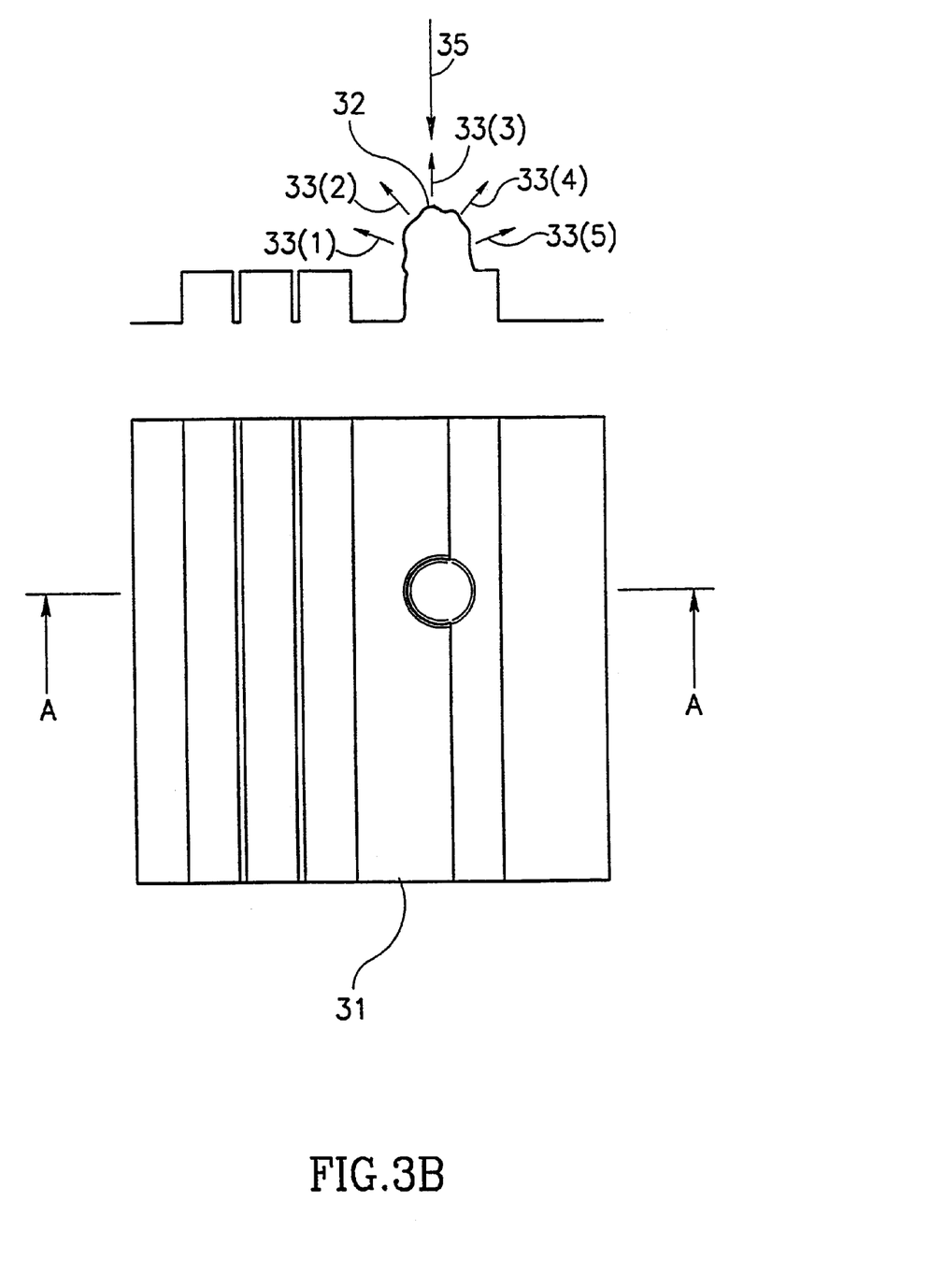

There follows a brief description of the so called scattered light attributes according to a specific embodiment of the invention which, as will be explained below, are used in the defect classification process. Attention is now directed to FIGS. 3A–B showing graphical representations of light scattering patterns as detected by respective, evenly distributed, dark field detectors in response to illuminating a particle (FIG. 3A) type defect. FIG. 3A shows a wafer (31) with a particle type defect adhered thereto (32) (shown in enlarged scale for the sake of clarity). A particle type defect is characterized by rising above the surface of the wafer. Due to the 3-dimensional (D) geometry of the particle and the irregular (non mirror like) surface thereof, the incident light beam is scattered in various directions as clearly shown in FIG. 3B. The latter illustrates, schematically a cross sectional side view of the wafer along A—A. Thus, light beam (35) that is incident on particle (32) is reflected in various directions (e.g. 36$^{(1)}$ 36$^{(2)}$ 36$^{(3)}$ 36$^{(4)}$ and 36$^{(5)}$. Turning back to FIG. 3A, the reflected light is detected by the four evenly distributed detectors ((26) (27) (28) and (29)—see FIG. 2) and the intensity (in terms of gray level) as detected by each detector is illustrated graphically in respective 3D graphs (36)–(39) in FIG. 3A. Each graph represents an X-Y matrix of pixels and the detected intensity (Z) expressed in 8-bit gray level value. As expected, higher energy (represented as a higher gray level value) is sensed by those pixels in a detector receiving light scattered from the particle (e.g. 36' in graph 36), compared to the energy sensed by those pixels which receive light reflected from the fault-free flat regions (e.g. 36" in graph 36).

Figure 4:
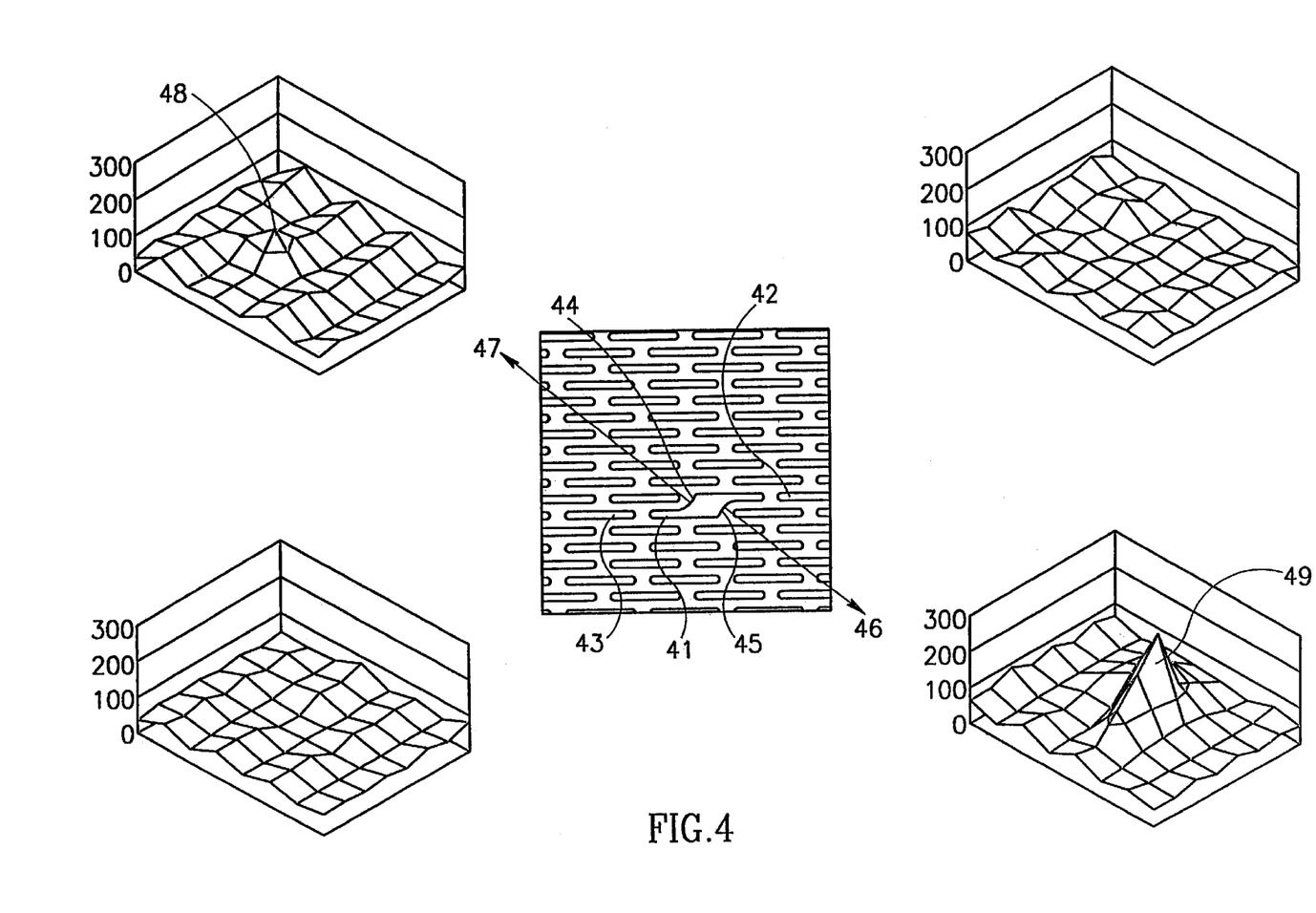
FIG. 4 is a graphical representation of a light reflection pattern as detected by respective evenly distributed dark field detectors in response to illuminating a pattern type defect.

Since light is scattered from the 3D particle in all directions, a particle type defect is detected as a high energy level, sensed by most or all of the detectors). A pattern type defect, in contrast, does not substantially rise above the surface of the inspected wafer. Thus, as shown in FIG. 4, a pattern type defect will normally give rise to detected high energy in only a few of the detectors. Hence, by way of example, defect (41) has an irregular pattern as compared to that of neighboring members (42 and 43). The irregular pattern (41) has inclined edges (44) and (45) which, when illuminated by the incident beam, will scatter reflects light in directions (46) and (47), which is detected as a high intensity in regions (48) and (49) of detectors (26) and (28) respectively.

Whilst the specific pattern and particle examples depicted in FIGS. 3 and 4 are, of course, not binding and numerous others may be encountered in real life scenario, they serve, generally, for understanding the distinction between pattern and particle type defects.

As explained above, in order to classify defects to certain categories, it is necessary to identify pixels originating from a defect. There are known in the literature techniques for accomplishing preliminary defect detection and a typical, yet not exclusive, technique is explained with reference to FIG. 5 (see also U.S. Pat. No. 5,699,447 to Alumot)

Figure 5:
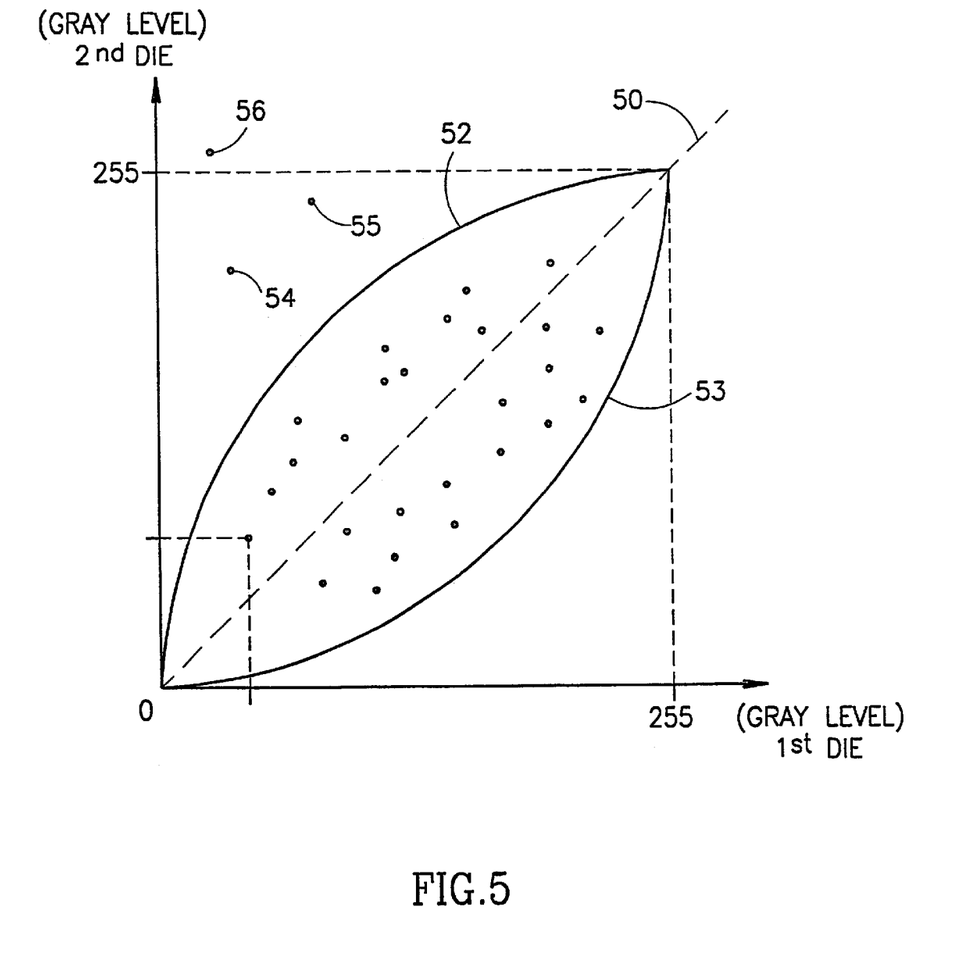
FIG. 5 is a graphic representation of one embodiment for identifying pixels of a defect.

Thus, FIG. 5 shows a graphic method for identifying pixels from a defect. The graph of FIG. 5 is constructed by plotting the gray level value of a pixel having (x,y) coordinates in a first die of an inspected wafer as a function of the gray level value of the pixel having the same (x,y) coordinates in a neighboring die. In the ideal case, (no defect), the two gray level values are equal and consequently all the points in Graph 5 lie on line (50). Put differently, the gray level value of the pixel in the first die (abscissa) is identical to the gray level value of the counterpart pixel in the neighboring die (ordinate). In reality, the points in the graph of FIG. 5 will be gathered around fine (50), and most of them will lie we the boundaries (52) and (53).

When a defect in a first die is encountered, a significant difference is detected between the gray level values of pixels originating from the defected region in first die and the gray level values of the counterpart pixels originating from the fault free region in a second die (for example, pixels 54, 55 and 56 that from part of a defect).

It should be noted that the graphic illustration of FIG. 5 is obtained by analyzing results obtained from one detector. As recalled, encountering defects in one detector does not necessarily imply that the same defect is encountered in the remaining detectors (see e.g. FIG. 4 where only two detectors detected the defect).

It should again be emphasized that the example of FIG. 5 is by no means binding and other techniques for detecting suspected defects are also feasible.

The following discussion will assist in understanding the specific scattered light attributes utilized for defect classification according to one embodiment of the invention, to wit:

Intensity: for all pixels classified by at least one detector as originating from a defect (or suspected of originating from a defect), sum the gray level values thereof so as to give rise to a total intensity value. Thus, for example, if 5 pixels in the first detector are classified as originating from a defect, and 6,8, and 5 pixels in respective second third and fourth detectors are, likewise, classified as originating from the defect, the total intensity value is calculated by summing the gray level values of the specified 24 pixels. Volume: the total number of pixels suspected of originating from defect in at least one detector. Thus, for example, if a given defect extends over 10 pixels in a first detector, 15 pixels in the second detector, 17 pixels in a third detector and none in the forth detector, the volume attribute is 10+15+17=42.

Linearity: this attribute grades how linear the array of defective pixels is in each detector. Thus, if all pixels suspected of originating from a defect lie (in a given detector) on a straight line, the linearity grade is 1. As the array of pixels deviates from a straight line, the linearity grade decreases Asymmetry: this attribute grades the symmetry of the defect by comparing the intensities of the scattered light detected by pairs of radially opposite placed detectors.

Figure 6:
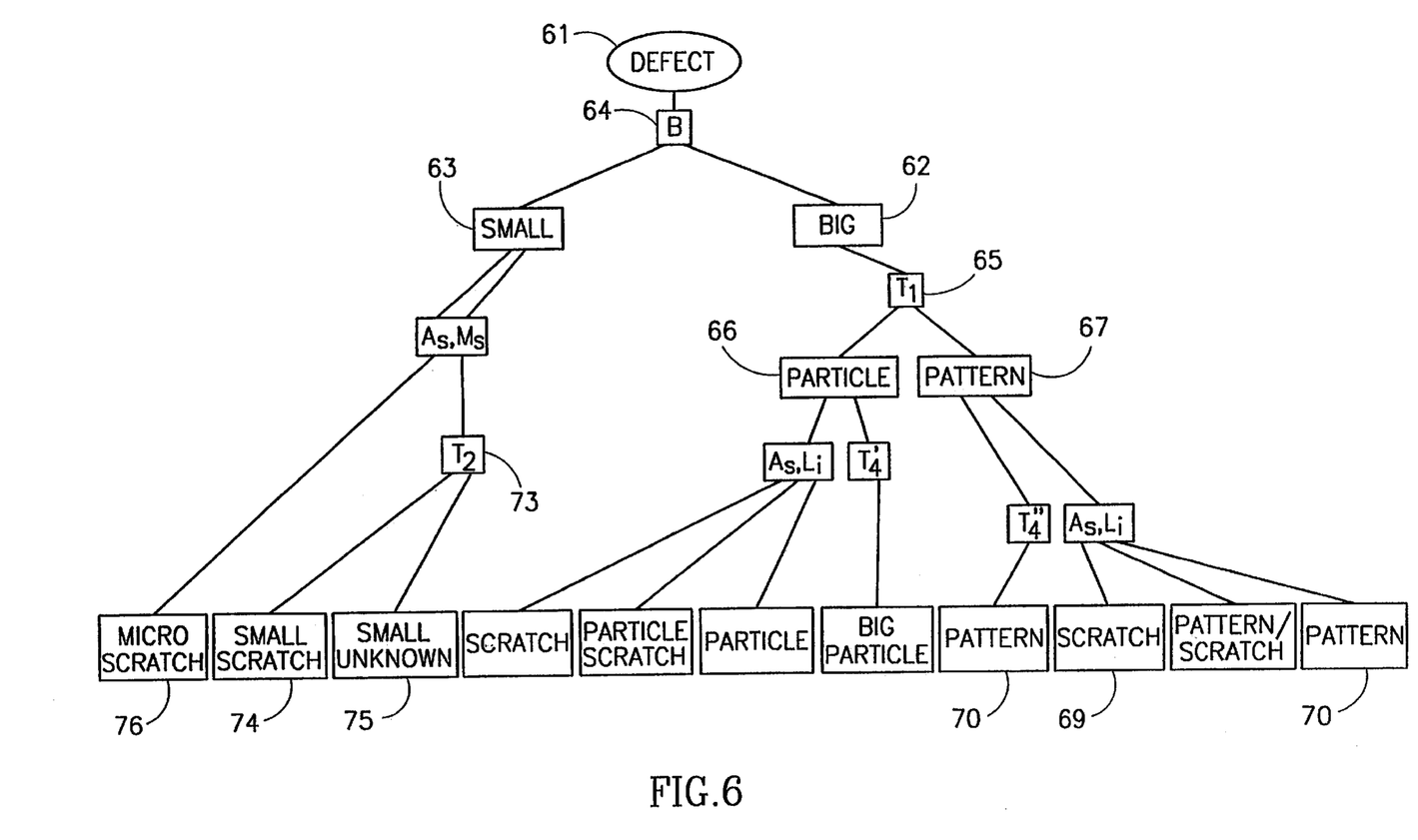
FIG. 6 is a block diagram illustrating a generalized defect classification analysis sequence, according to one embodiment of the invention.
Figure 7:
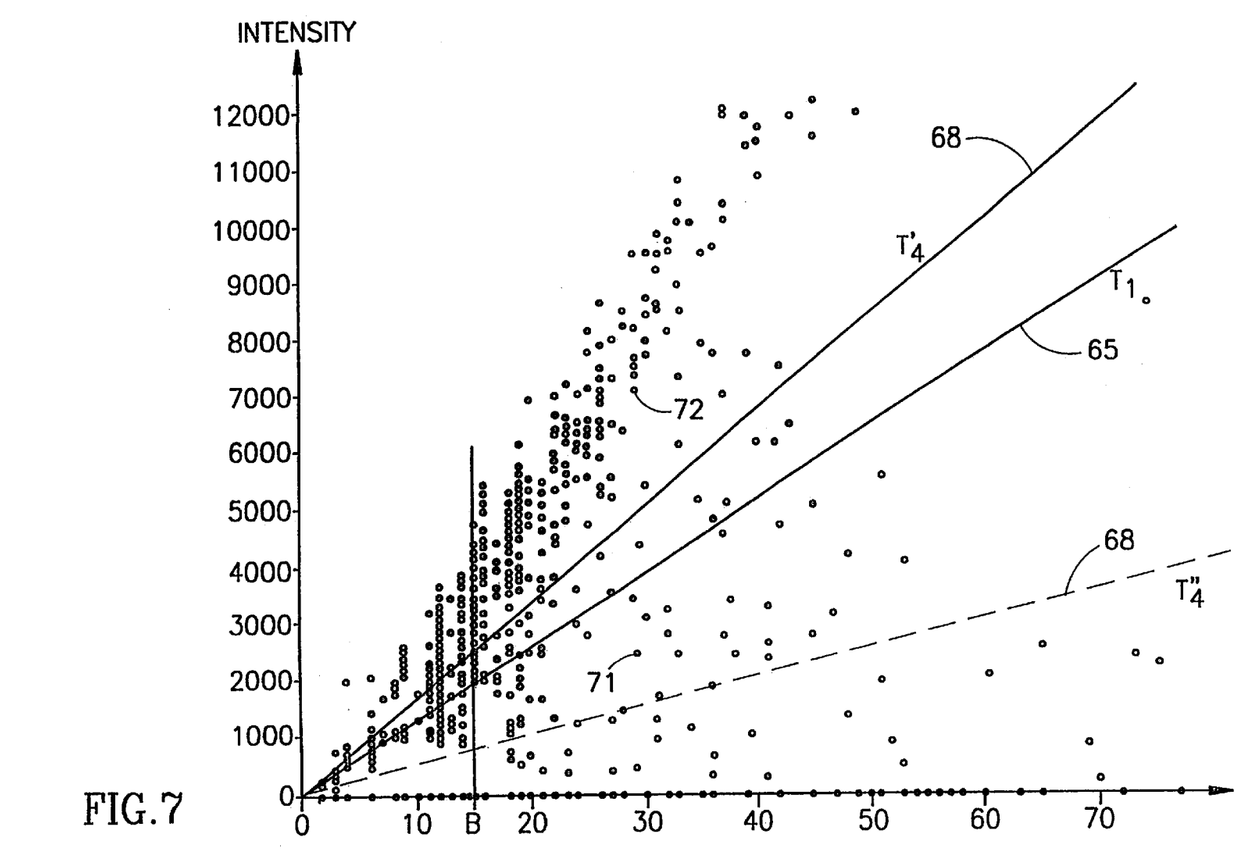
FIG. 7 is a graph repesenting volume vs. intensity attributes that is utilized in a defect classification analysis procedure, according to one embodiment of the invention.

Having described, in general, the scattered light attributes according to one embodiment of the invention, there follows a description, with reference to FIGS. 6 and 7, of a sequence of steps for performing defect classification.

It should be emphasized that after having detected pixels constituting a defect (e.g. by utilizing the technique of FIG. 5), the specified attributes are utilized for defect classification whilst the wafer is still under inspection (i.e. "on the fly").

Turning now to FIG. 6, a defect (61) is classified as Big (62) or Small (63) according to whether its volume attribute is smaller or larger than a threshold value B. In is specific example the threshold B is set to 16. For "Big" defects (62), a further analysis step which exploits a first threshold T1 (65) aims at distinguishing between a Particle type defect (66) and a Pattern type defect (67). As recalled, a particle has a substantially three-dimensional geometry, whereas a pattern has a substantially two-dimensional geometry. For a better understanding of the foregoing, attention is now directed to FIG. 1 showing a graphic representation of volume (abscissa) vs. intensity (ordinate) attributes. Distinguishing between a pattern and a particle is based on the observation that for a given volume attribute (i.e. number of pixels that constitute a defect), the intensity grade associated with a particle is, as a rule, higher than that associated with a pattern. This is due to the fact that particles tend to scatter the incident light in all directions and consequently, a high intensity is sensed in all detectors. In contrast, a pattern type defect of the same size (i.e. having the same volume value) tends to scatter the incident light in particular directions, so that only some of the detectors sense a high intensity (see e.g. FIG. 3A–B vs. 4). Thus, for a given defect size, a particle will give rise to a higher intensity attribute than a pattern.

This observation is clearly reflected in FIG. 7, where for "Big" volumes (i.e. exceeding the threshold B (64)), those defects lying above threshold T1 (65) are classified as particles whereas those residing below T1 are classified as patterns. Thus, for example, defects (71) and (72) both have the same volume grading 30, but respective intensity values of 2200 (below threshold T1) and 6800 (above threshold T1). Accordingly, the former is classified as a pattern and the latter a particle.

Reverting now to FIG. 6, T4 (68) provides an additional fine tuning tool. Thus, T4 can be placed between the abscissa and T1(designated T4" in FIG. 6) or above T1(designated T4' in FIG. 6). In the former option, T4" assists in discerning between scratches and patterns. Thus, all the population of suspected defects that reside below T4" is classified as patterns (70 in FIG. 6) whereas the population of patterns that reside between T4" and T1 is subject to further analysis in order to distinguish between pattern and scratch. (see below). This decision criterion is based on the assumption that for a given volume, patterns will generate lower intensity than scratches and therefore all those population who generate low intensity for a given volume (i.e. they reside below T4").

Now, The asymmetry and linearity attributes will assist in refined classification patterns into scratch type defects and pattern type defects. The underlying premise in distinguishing scratches from patterns is that scratches are linear whereas other pattern type defects are round. The linearity-asymmetry criterion is applied only to those populations that reside between T4" and T1.

Figure 8:
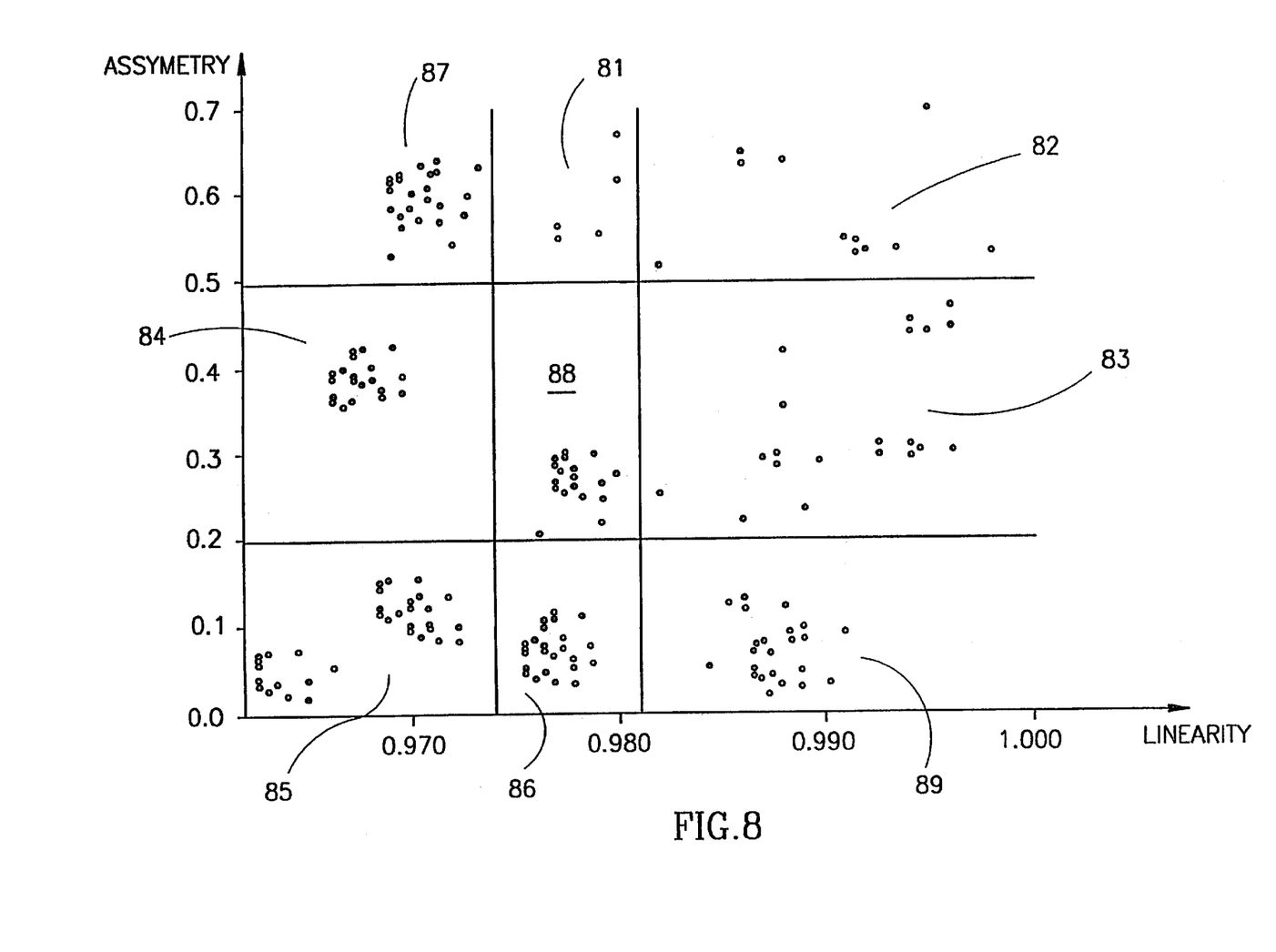
FIG. 8 is a graph of asymmetry vs. linearity attributes that is utilized in the defect classification analysis procedure, according to one embodiment of the invention.

Bearing this general observation in mind, attention is now directed to FIG. 8, which will assist in clarifying the distinctions between scratches and patterns. The abscissa in FIG. 8 is the linear regression coefficient wherein 1 indicates perfect linear and 0 random scattering. In the graph of FIG. 8, the asymmetry values range from 0 to 0.7. The asymmetry value is obtained according to the following algorithmic expression: 1−(A+B/C+D)

where A, B are the intensities detected by respective members of a first pair of opposite detectors (e.g. 27 and 29 in FIG. 2) and C, D are the intensities detected by respective members of a second pair of opposite detectors (e.g. 26 and 28 in FIG. 2).

Thus, for example, defect (41) in FIG. 2 is asymmetric as it scatters light only in the directions of one pair of detectors and virtually does not reflect light in the direction of the other pair. The ratio A+B/C+D is thus small and the overall result 1−(A+B/C+D) is, obviously, close to 1.

Accordingly, the more asymmetry is the attribute of the defect the closer is the asymmetry grading to 1.

In FIG. 8, areas (81, 82 and 83) are characterized by high linear and asymmetric grading and therefore defects residing therein are classified as scratches (69 in FIG. 6). Defects residing in areas (84, 85 and 86), are characterized by low linearity and a high symmetric grading ((70) in FIG. 6) and are therefore classified as patterns.

The rest of the areas (87), (88) and 89) are equivocally classified as scratch or pattern.

It should be noted that various modifications may be applied. Thus, by way of a non limiting example, the thresholds which distinguish between the specified areas (0.2 and 0.5 in the ordinate) and (0.974 and 0.982 in the abscissa may be set to different values and, likewise, the number of areas may be changed, all as required and appropriate.

T4' serves for fine tuning decision criteria between big particle and scratches. Thus, all the population of defects that reside above T4' is classifies as big particles (since for a given volume they generate a very high intensity), whereas the population that reside between T1 and T4' is send to the asymmetry-linearity decision phase for classifying the defects as scratch, big particle or not decided (i.e. scratch or big particle).

Turning now to small defects (63 in FIG. 6), due to their small geometry, it is difficult to apply the intensity/volume criteria used for big defects to discern between 3D particle) and 2D (pattern) defects. Thus, a second threshold T2 (73), serves for distinguishing between small particle (74) and small unknown (75). As before, 72 is determined empirically depending upon the particular application.

Now, the distinction between small pattern (74) and micro-scratch (76) obtained according to the asymmetric grading, i.e. symmetric defects are classified as small particle whereas asymmetric defects are classified as micro-scratches. Due to the small dimension of the defect, use of the linearity attribute to distinguish between micro scratches and small particles is unreliable and therefore not used.

Those versed in the art will readily appreciate that the definition of the scattered light attributes may be modified, one or more attributes may be deleted and/or others may be added, all as required and appropriate depending upon the particular application. Likewise, the utilization of scattered light attributes for classifying defects is by no means bound to the specific examples illustrated with reference to FIGS. 6 to 8. Put differently, the attributes may be utilized in a different manner for classifying the specified defects, one or more of the classifications may be modified, one or more classifications may be deleted and/or others may be added, all as required and appropriate. One, non-limiting, modification concerns utilization of at least one additional bright field detector (not shown). By this specific embodiment, the bright field detector contributes only to the volume attribute in that the number of pixels detected by the bright field detector (and which are suspected to originate from a defect) is summed to together with the counterpart numbers of pixels a contributed by the dark field detectors so as to constitute a volume value. Thus, the volume attribute will consist on the sum of pixels that form part of a defect in all the dark field detectors and in the bright field detector. The utilization of the bright field by this specific embodiment is based on that unlike dark field detectors, which sense energy reflected from only parts of the defect under question, bright field detector is placed above the defect and therefore has a clearer view of the entire defect or at least a major portion thereof.

By this specific example, the bright field detector does not contribute to the other attributes (intensity, linearity and asymmetry).

Figure 9:
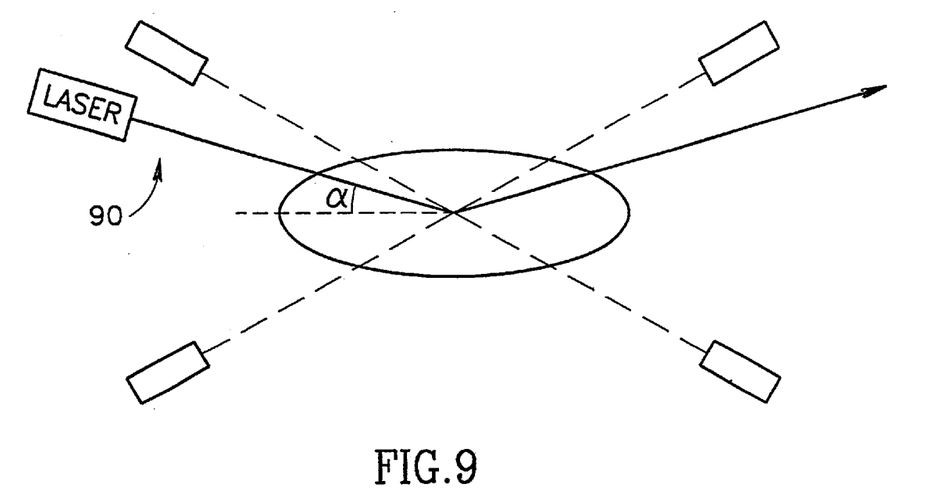
FIG. 9 is a schematic block diagram of a system according to another embodiment of the invention.
Figure 10:
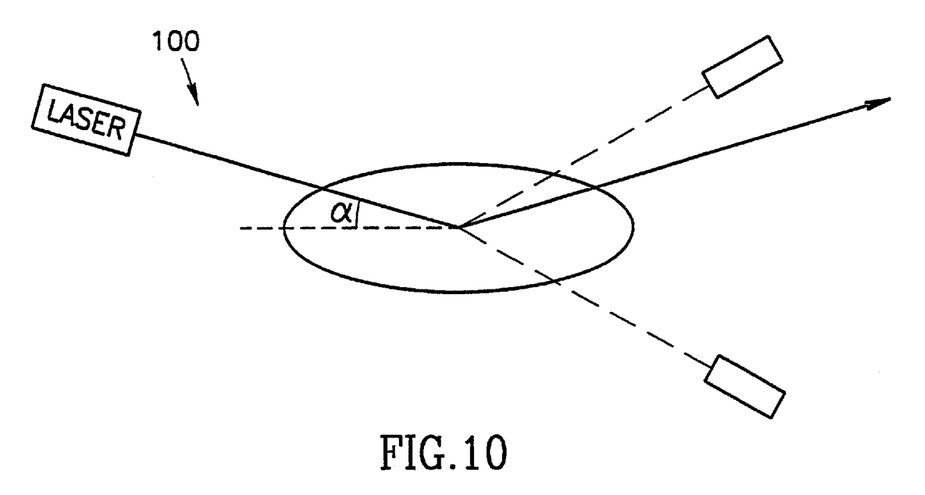
FIG. 10 is a schematic block diagram of a system according to yet another embodiment of the invention.

Another non-limiting modification is illustrated in reference to FIG. 9, where unlike FIG. 2, the illuminating beam (90) is incident on the wafer at an angle α substantially different than 90°. FIG. 10 illustrates yet another non limiting modification where the illuminating beam (100) is incident on the wafer at an angle α substantially different than 90°, and only two dark field detectors are utilized. Generally speaking, the exploitation of intensity, volume, asymmetry and linearity characteristics as generally illustrated and described with reference to FIG. 6 may be used in a similar manner also for the configurations of FIG. 9 and/or 10. This, however, is not obligatory.

It should be noted that designation of order of steps in the claims are done for convenience only.

The present invention has been described with a certain degree of particularity but it should be understood that various modifications and alterations may be made without departing from the scope or spirit of the invention as defined by the following claims:

What is claimed is:

1. A method for on-the-fly automatic defect classification (ADC) in a scanned substrate, comprising:
   (a) providing at least two spaced apart detectors;
   (b) illuminating the scanned substrate so as to generate an illuminating spot incident on the substrate;
   (c) collecting light scattered from the spot by at least two spaced apart detectors;
   (d) analyzing said collected light so as to detect defects in said substrate; and
   (e) classifying said defects into distinct defect types by analyzing scattered light volume attribute and at least one other attribute of said collected light;
   wherein said step for analysis for classifying defects utilizing scattered light attributes includes at least one of the following attributes: scattered light intensity, scattered light linearity and scattered light asymmetry.

2. A system for on-the-fly automatic defect classification (ADC) in a inspected substrate, comprising:
   (a) light source illuminating the inspected substrate;
   (b) at least two spaced apart detectors situated to receive light scattered from the substrate and generating corresponding signals;
   (c) a processor analyzing said signals so as to detect defects in said substrate; and
   (d) a defect classifier analyzing scattered light volume attribute and at least one other attribute of said signals and classifying said defects into distinct defect types; wherein said attributes correspond to at least one of the following attributes: scattered light intensity, scattered light linearity and reflected light asymmetry.

3. The system of claim 2, wherein said intensity and volume attributes are utilized for defining a first threshold; said classifier classifying said defects into particle type or pattern type per said first threshold.

4. The system of claim 3, wherein said intensity and volume attributes are further utilized for defining a second threshold; said classifier of utilizing said second threshold for classifying said pattern defects into pattern type defect or scratch type defect.

5. The system of claim 3, wherein said intensity and volume attributes are further utilized for defining a second threshold; said classifier utilizing said second threshold for classifying said particle defects into big particle type or scratch\particle type defect.

6. The system of claim 2, wherein said classifier utilizes said asymmetry and linearity attributes for classifying pattern type defect into scratch type defect or pattern type defect; said classifier further utilizes said asymmetry and linearity attributes for classifying particle type defect into particle type or scratch type defect.

7. A method for on-the-fly automatic defect classification (ADC) in a scanned substrate, comprising:
   (a) providing at least two spaced apart detectors;
   (b) illuminating the scanned substrate so as to generate an illuminating spot incident on the substrate;
   (c) collecting light scattered from the spot by the at least two spaced apart detectors;
   (d) analyzing said collected light so as to detect defects in said substrate and classifying said defects into distinct defect types; and
   (e) classifying said defects into defect types by analyzing a scattered light volume attribute and at least one other attribute of said collecting light.

8. The method of claim 7, wherein said step (a) comprises providing at least four spaced apart dark field detectors.

9. The method of claim 8, wherein said step (a) comprises arranging said detectors such that each detector faces another detector located substantially opposite thereto.

10. The method of claim 8, wherein said step (a) comprises arranging said detectors in a substantially uniform distribution around the scanned substrate.

11. The method of claim 8, further comprising the steps of providing at least one additional bright field detector; reflected light being collected by said additional at least one bright field detector according to step (c) and said analysis, stipulated in said step (d), being applied to the reflected light collected by said additional at least one detector.

12. The method according to claim 8, wherein said step of classifying includes at least two of the following types: small particle, big particle; small pattern, big pattern; small scratch, big scratch.

13. The method of claim 7, wherein said step (a) comprises arranging said detectors such that the optical axis of each detector is at a grazing angle to the surface of the inspected substrate.

14. The method of claim 7, wherein said step (b) comprising illuminating the substrate such that said spot is incident on the substrate at a grazing angle to the substrate surface.

15. The method of claim 7, further comprising the steps of providing at least one additional bright field detector; reflected light being collected by said additional at least one bright field detector according to step (c) and said analysis, stipulated in said step (d), being applied to the reflected light collected by said additional at least one detector.

16. The method of claim 7, wherein said dark field detectors are arranged symmetrically about at least one axis.

17. The method of claim 7, wherein said steps for analyzing and classifying defects utilizes the scattered light volume attribute and comprises at least one of the following attributes: scattered light intensity, scattered light linearity and scattered light asymmetry.

18. The method according to claim 7, wherein said step of classifying includes at least two of the following types: small particle, big particle; small pattern, big pattern; small scratch, big scratch.

19. A system for on-the-fly automatic defect classification (ADC) in an inspected substrate, comprising:
   (a) light source illuminating the inspected substrate;
   (b) at least two spaced apart detectors situated to receive light scattered from the substrate and generating corresponding signals;
   (c) a processor analyzing said signals so as to detect defects in said substrate; and
   (d) a defect classifier analyzing a scattered light volume attribute and at least one other attribute of said signals and classifying said defects into distinct defect types.

20. The system of claim 19, wherein said at least two spaced apart detectors are arranged symmetrically about at least one axis.

21. The system of claim 20, wherein said classifier classifies said defects into at least two of the following types: small particle, big particle; small pattern, big pattern; small scratch, big scratch.

22. The system of claim 19, wherein said detectors are arranged such that each detector faces another detector located substantially opposite thereto.

23. The system of claim 19, wherein said detectors are arranged in a substantially uniform distribution around the scanned substrate.

24. The system of claim 19, wherein said detectors are arranged such that the optical axis of each detector is at a grazing angle to the surface of the inspected substrate.

25. The system of claim 19, wherein said light source illuminates the substrate at a grazing angle.

26. The system of claim 25, further comprising at least one bright field detector.

27. The system of claim 19, further comprising at least one bright field detector.

28. The system of claim 19, further comprising a first and a second thresholds, and wherein said defect classifier analyzes the signals with respect to said first threshold to differentiate between small and large defects, and analyzes the signals with respect to said second threshold to differentiate between pattern and particle defects.

29. The system of claim 19, wherein said at least one other attribute corresponds to at least one of the following attributes: scattered light intensity, scattered light linearity and reflected light asymmetry.

30. The system of claim 29, wherein said intensity and volume attributes are utilized for defining a first threshold; said classifier classifying said defects into particle type or pattern type per said first threshold.

31. The system of claim 30, wherein said intensity and volume attributes are further utilized for defining a second threshold; said classifier utilizing said second threshold for classifying said pattern defects into pattern type defect or scratch type defect.

32. The system of claim 30, wherein said intensity and volume attributes are further utilized for defining a second threshold; said classifier utilizing said second threshold for classifying said particle defects into big particle type or scratch\particle type defect.

33. The system of claim 29, wherein said classifier utilizes said asymmetry and linearity attributes for classifying pattern type defect into scratch type defect or pattern type defect; said classifier further utilizes said asymmetry and linearity attributes for classifying particle type defect into particle type or scratch type defect.

34. The system according to claim 19, wherein said classifier classifies said defects into at least two of the following types: small particle, big particle; small pattern, big pattern; small scratch, big scratch.

35. In a system for on-the-fly automatic defect classification (ADC) in a scanned wafer, a processor programmed to perform the steps comprising:
   receiving signals from at least two spaced apart detectors, which signals are indicative of light scattered from the wafer and detected by said detectors; and
   analyzing a scattered light volume and at least one other attribute of said signals so as to detect defects in said wafer and classifying said defects into distinct defect types.

36. An inspection system for inspecting substrates for defects, comprising:
   a light source illuminating said substrate;
   at least two detectors situated to detect light scattered from the substrate and generate at least a first and second inspection signals;
   a comparator receiving and comparing said at least first and second inspection signals to at least a first and second reference signals, respectively, to detect defects in said substrate and identify defect locations;
   a classifier receiving said at least said first and second inspection signals and analyzing a scattered light volume and at least one other attribute of said at least first and second inspection signals corresponding to said defect locations, and classifying said defects according to said attributes.

37. The inspection system of claim 36, wherein said at least one other attribute is selected from: intensity, linearity, and asymmetry.

38. The inspection system of claim 36, wherein intensity is obtained by summing intensities of said at least first and second inspection signals.

39. The inspection system of claim 36, wherein the scattered light volume is obtained by summing a number of pixels of said at least first and second inspection signals which correspond to a defect location.

40. The inspection system of claim 36, wherein linearity is obtained by determining alignment of pixels in said at least first and second inspection signals corresponding to defect locations.

41. The inspection system of claim 36, wherein asymmetry is obtained by comparing intensity levels of said at least first and second inspection signals corresponding to defect locations.

* * * * *